United States Patent [19]

Cragoe, Jr. et al.

[11] 4,377,588

[45] Mar. 22, 1983

[54] 4-(SUBSTITUTED THIAZOLYL)-3-HYDROXY-3-PYRROLINE-2,5-DIONE INHIBITORS OF GLYCOLIC ACID OXIDASE

[75] Inventors: Edward J. Cragoe, Jr., Lansdale; Clarence S. Rooney, Worcester, both of Pa.; Haydn W. R. Williams, Dollard des Ormeaux, Canada

[73] Assignees: Merck Sharp & Dohme (I.A.) Corp.; Merck & Co., Inc., both of Rahway, N.J.

[21] Appl. No.: 74,468

[22] Filed: Sep. 11, 1979

[51] Int. Cl.³ .................. A61K 31/425; C07D 417/04
[52] U.S. Cl. .................................... 424/270; 548/203; 548/204
[58] Field of Search ................ 548/204, 203; 424/270

[56] References Cited

U.S. PATENT DOCUMENTS 2,870,158  1/1959  Asinger et al. .................. 548/202
3,340,263  9/1967  Stachellh et al.
3,418,332  12/1968  Davis et al. .................. 548/202

OTHER PUBLICATIONS

Liao et al., Arch. Biochem. Biophys., 154, pp. 68–75 (1973).
Harlay, J. Pharm. Chim., 24, pp. 537–548 (1936).
Randall et al., J. Med. Chem., 22, pp. 608–614 (1979).
G. S. Skinner et al., J. Am. Chem. Soc., 73, pp. 2230–2233 (1951).
G. S. Skinner et al., J. Am. Chem. Soc., 70, pp. 4011–4013 (1948).

*Primary Examiner*—Donald G. Daus
*Assistant Examiner*—D. B. Springer
*Attorney, Agent, or Firm*—Raymond M. Speer; Michael C. Sudol, Jr.

[57] ABSTRACT

Novel 4-(substituted thiazolyl)-3-hydroxy-3-pyrroline-2,5-diones are disclosed which inhibit glycolic acid oxidase and thus are useful in the treatment and prevention of calcium oxalate renal lithiasis.

7 Claims, No Drawings

4-(SUBSTITUTED THIAZOLYL)-3-HYDROXY-3-PYRROLINE-2,5-DIONE INHIBITORS OF GLYCOLIC ACID OXIDASE

BACKGROUND OF THE INVENTION

Close to 70% of kidney stones in man are composed partially or predominantly of calcium oxalate. There is no satisfactory drug specific for the treatment of calcium oxalate renal lithiasis, nor for prophylactic use by patients prone to recurrent attacks of this disease.

The most common treatment for renal lithiasis due to calcium oxalate consists of surgical removal of stones, control of the diet to restrict calcium or oxalate, and ingestion of large quantities of water to dilute the urine. Attempts at chemotherapy have included the administration of magnesium oxide, calcium carbimide, orthophosphate, cellulose phosphate, isocarboxazide, thiazide diuretics, allopurinol and succinimide. Limited success has been realized by these drug approaches. No drug which specifically inhibits the biosynthetic formation of oxalic acid has previously been developed for the treatment of calcium oxalate renal lithiasis.

The immediate metabolic precursor of the majority of the oxalate in the urine of a typical patient is glyoxylic acid. In turn its most important precursor is glycolic acid. The enzyme glycolate oxidase is able to carry out the oxidation of glycolic acid, through glyoxylic acid, to oxalic acid. Inhibition of this enzyme will, therefore, reduce the concentration of oxalic acid in the kidney and bladder, reducing the probability that calcium oxalate crystallization will occur. Thus inhibitors of glycolate oxidase provide a specific approach to the prevention and treatment of calcium oxalate renal lithiasis.

Liao, et al, *Arch. Biochem. Biophys.*, 154, 68–75 (1973) have shown that phenyllactic acid and n-heptanoic acid, which are inhibitors of glycolate oxidase, inhibit oxalate biosynthesis in isolated perfused rat liver. These compounds are not sufficiently potent to be useful as drugs.

The preparation of 3-hydroxy-4-phenyl-3-pyrroline-2,5-dione

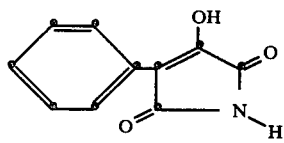

has been described by Harlay, *J. Pharm. Chim.*, 24, 537-48 (1936). 3-Hydroxy-4-aryl-3-pyrroline-2,5-diones are described in U.S. Pat. No. 3,349,263 as intermediates in the preparation of antiphlogistic substances. A number of 3-hydroxy-4-substituted phenyl-3-pyrroline-2,5-diones are reported by G. S. Skinner, et al., *J. Am. Chem. Soc.*, 73, 2230 (1951). (In this paper these compounds are referred to as pyrrolidine-2,3,5-trione derivatives). 3-Hydroxy-4-(4-bromo-1-naphthyl)-3-pyrroline-2,5-dione is described by G. S. Skinner, et al., *J. Am. Chem. Soc.*, 70, 4011 (1948).

SUMMARY OF THE INVENTION

It has now been found that novel compounds of the formula:

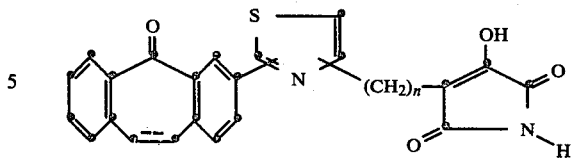

wherein
n is 0 to 2;
or pharmaceutically acceptable salts thereof, with the proviso that the substituents on the thiazolyl ring are not adjacent, are potent inhibitors of glycolate oxidase. They are, therefore, useful in the treatment and prevention of calcium oxalate kidney and bladder stone formation.

Preferred compounds are those wherein n is 0; having the structure:

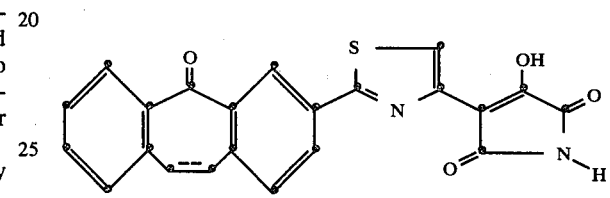

wherein the dotted line indicates saturation or unsaturation.

DETAILED DESCRIPTION

About 70% of all renal calculi contain oxalate as the main component of the matrix. In the majority of patients the condition is associated with a higher than average level of metabolically produced oxalate. The major pathway for biosynthesis of oxalate can be represented as follows:

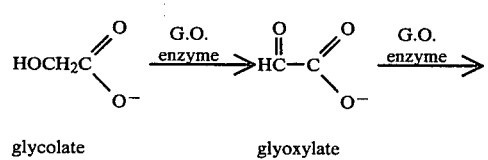

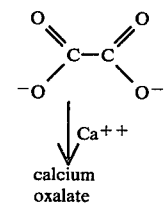

calcium oxalate

Glyoxylate is the major immediate forerunner of oxalate. An inhibitor of glycolate oxidase (G.O.) will inhibit both the conversion of glyoxylate to oxalate as well as the production of glyoxylate from glycolate. By reducing oxalic acid levels in the urine with the compounds of this invention, the formation or oxalate calculi will be reduced or prevented.

Compounds of formula (I) are potent inhibitors of glycolate oxidase and thus are useful in restricting oxalate levels in the blood and urine. Further, they are useful in the treatment and prevention of renal disease due to calcium oxalate stone formation in the kidney and bladder. They may be useful in the treatment of the genetically inherited diseases termed Hyperoxaluria types I and II in which very high levels of metabolic oxalic acid are present.

Compounds of formula (I) have been unexpectedly found to block the contractions of guinea pig ileum induced by Slow Reacting Substance of Anaphylaxis (SRS-A). They are ineffective against contractions caused by histamine, which demonstrates specificity against SRS-A. SRS-A is considered a major mediator in human allergic asthma. Thus the compounds of formula (I) are useful in the treatment of allergy, especially allergic asthma.

Compounds of formula (I) can be prepared according to the following routes:

Route I

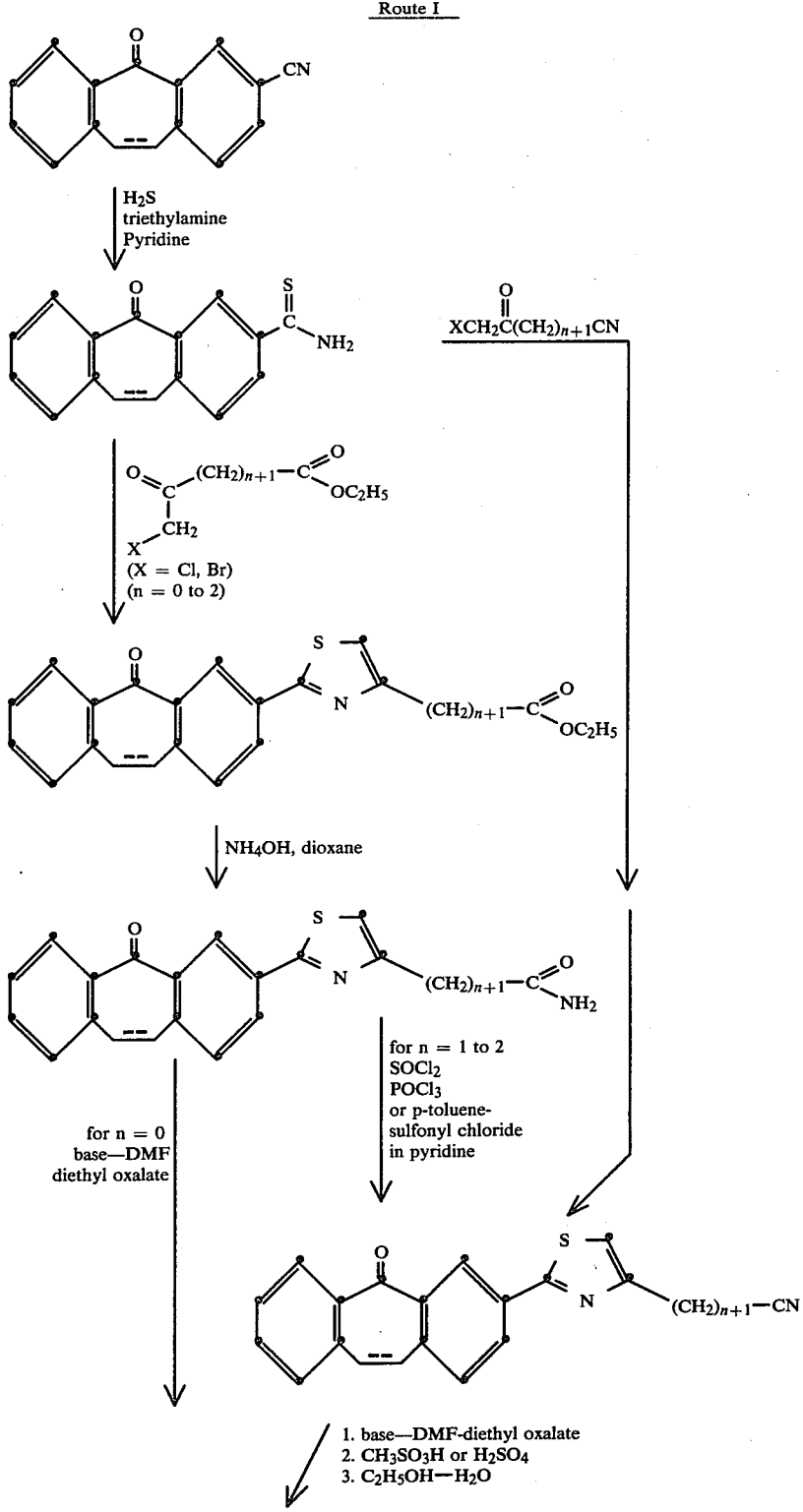

-continued
Route I
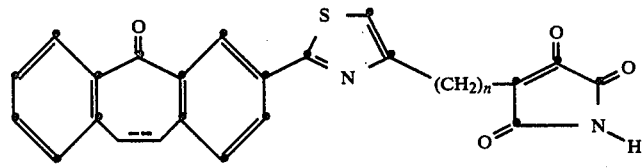
ROUTE II
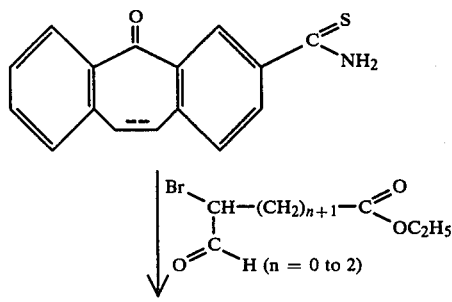
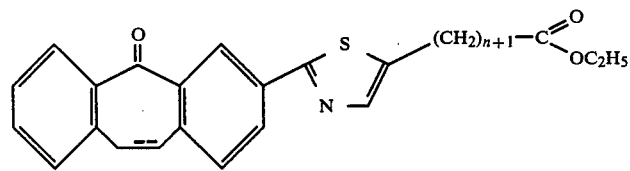
↓ NH₄OH, dioxane
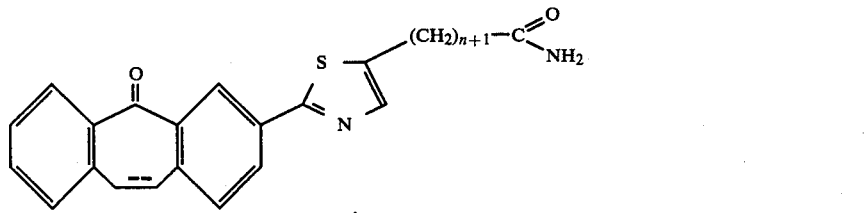
for n = 0 base
DMF diethyl oxalate
for n = 0 to 2
SOCl₂, POCl₃
or p-toluene-
sulfonyl chloride
in pyridine (—H₂O)
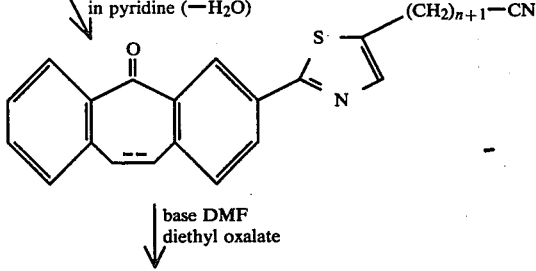
base DMF
diethyl oxalate -continued
ROUTE II
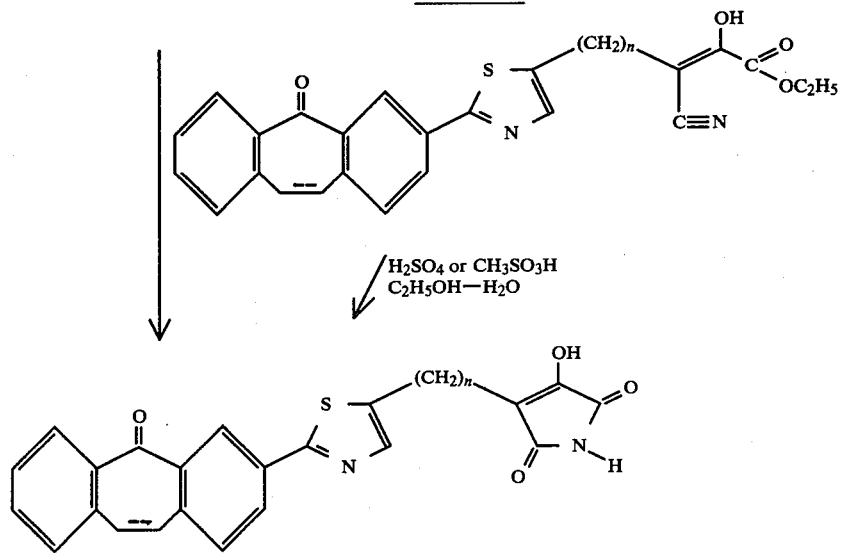
ROUTE III
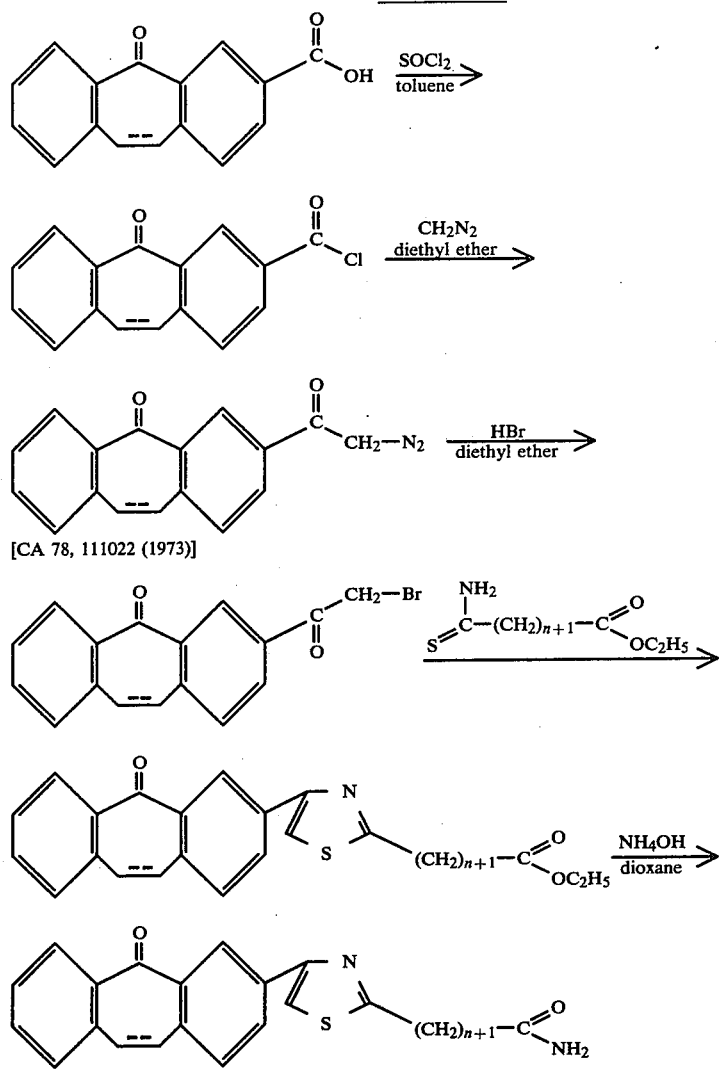
[CA 78, 111022 (1973)]

ROUTE III

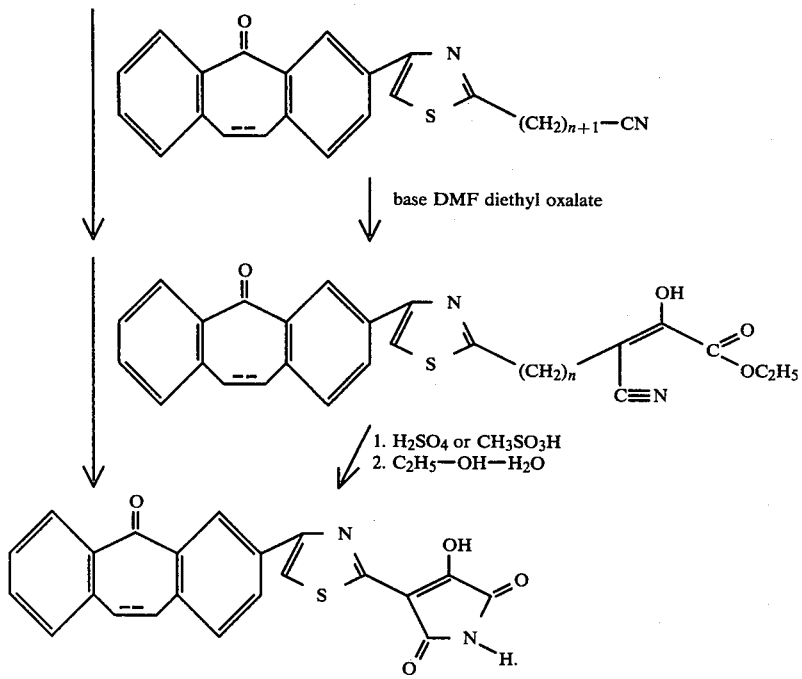

In the preparation of thiazole derivatives with the dibenzo[a,d]cycloheptene substituent at the 2-position and the hydroxypyrrolinedione moiety attached at the 4- or the 5-position, the starting material is the appropriate nitrile derivative of the tricyclic system. Conversion of the nitrile to the thioamide is carried out by procedures well known in the art, such as hydrogen sulfide in pyridine in the presence of triethylamine. Reaction of the thioamide intermediate with 4-chloroacetoacetic acid ethyl ester in refluxing alcoholic solvent gives directly the 2-(dibenzo[a,d]cycloheptenyl)thiazole-4-acetic acid ethyl ester. The ethyl ester is converted to the amide by reaction with concentrated ammonium hydroxide in dioxane at temperatures from room temperature to 60° C. for periods of 24 hours to 5 days (or with methanol saturated with ammonia). The resultant amide intermediates are reacted with diethyl oxalate in solvents such as DMF, toluene, ethanol in the presence of strong base such as potassium t-butoxide, sodium ethoxide or lithium diisopropylamide at a temperature from 0°–80° C. for periods of 5 to 48 hours. Acidification of the reaction mixture permits the isolation of the desired derivatives of formula (I) wherein n=0, and the hydroxypyrrolinedione moiety is attached at the 4-position of the thiazole ring.

For analogous compounds wherein n=1 or 2, the homologs of 4-chloroacetoacetic acid ethyl ester are employed [e.g., 5-chloro(or bromo)-4-oxopentanoic acid ethyl ester for n=1, and 6-chloro(or bromo)-5-oxohexanoic acid ethyl ester for n=2] in the thiazole-forming step. Amide formation is as described above. For the synthesis of the hydroxypyrrolinedione derivative of formula (I) wherein n=1 or 2, the corresponding nitriles are required as intermediates for the reaction with diethyl oxalate. The homologous amides are converted to nitriles by methods well known in the art, such as p-toluenesulfonyl chloride or methanesulfonyl chloride in pyridine, thionyl chloride and phosphorus oxychloride either neat with heating, or in DMF or pyridine or dicyclohexylcarbodiimide in pyridine, or titanium tetrachloride and N-methylmorpholine in dry tetrahydrofuran. An alternative more direct route involves use of the appropriate 2-halomethylketoalkanenitrile in the reaction with the thioamide intermediate. Reaction of the homologous nitriles with diethyl oxalate is carried out in solvents such as DMF, toluene or ethanol with strong base, usually sodium or potassium alkoxides. The 3-cyano-2-ketoester intermediate thus formed is converted to the hydroxypyrrolinedione derivative of formula (I) by first dissolving in sulfuric acid or methanesulfonic acid and allowing to stand at 0° C. to room temperature overnight. The reaction when quenched with ethanol-water or ice-water gives the 3-hydroxy-3-pyrroline-2,5-dione derivative (I) wherein n=1 or 2 with the hydroxypyrrolinedione moiety at the 4-position of the thiazole ring.

For the synthesis of (I) derivatives with the hydroxypyrrolinedione moiety attached at the 5-position of the thiazole ring the above procedures are followed with the exception that for the thiazole ring forming step there is utilized instead of the α-haloketone, the isomeric α-haloaldehydicalkanoic ester intermediates. For example, in place of 4-chloroacetoacetic acid ethyl ester, 4-oxo-3-bromobutyric acid ethyl ester is employed.

For the synthesis of (I) derivatives in which the dibenzo[a,d]cycloheptene substituent is located at the 4-position of the thiazole ring and the hydroxypyrrolinedione moiety connected through the 2-position of the thiazole ring, a slightly different sequence of reactions is required. The dibenzocycloheptene carboxylic acid starting material is converted to the acid chloride by standard methods (e.g., thionyl chloride in DMF or oxalyl chloride). Reaction of the acid chloride with diazomethane in diethyl ether at room temperature provides the diazoketone intermediate which is converted to the bromomethyl ketone by reaction with anhydrous HBr in ether. The dibenzo[a,d]cycloheptenylbromomethyl ketone is allowed to react with an appropriate ethoxy carbonyl alkyl thioamide to form the 4-(dibenzo[a,d]cycloheptenyl)-2-thiazolyl alkanoic acid ethyl ester intermediate which is then converted to the amide and subsequently to the hydroxypyrrolinedione derivatives by procedures outlined above.

EXAMPLE 1

Preparation of 4-[2-(10,11-Dihydro-5H-5-oxodibenzo[a,d]cyclohepten-3-yl)-4-thiazolyl]-3-hydroxy-3-pyrroline-2,5-dione

Step 1:
10,11-Dihydro-5H-5-oxodibenzo[a,d]cycloheptene-3-thioamide

Hydrogen sulfide gas from a lecture cylinder is passed through pyridine (50 ml) for 15 minutes. Triethylamine (30 mil) and 10,11-dihydro-5H-5-oxodibenzo[a,d]-cycloheptene-3-carbonitrile (6.8 g, 0.029 mole) is added. Passage of hydrogen sulfide gas into the mixture is continued for 3 hours. After standing at room temperature overnight air is passed through the mixture for 15 minutes. The reaction mixture is poured into icewater (500 ml). The product is extracted into diethylether (3×200 ml). After washing with water (3×200 ml) and drying (Na$_2$SO$_4$), and evaporation of the diethylether there was obtained 5.7 g of the title compound, m.p. 138°–140° C. A sample recrystallized from ethanol had m.p. 141°–143° C.

Elemental analysis for C$_{16}$H$_{13}$NOS: Calcd.: C, 71.58; H, 4.90; N, 5.24; Found: C, 71.68; H, 4.91; N, 5.13.

Step 2:
2-(10,11-Dihydro-5H-5-oxodibenzo-[a,d]cyclohepten-3-yl)thiazole-4-acetic acid ethyl ester A mixture of 10,11-dihydro-5H-5-oxodibenzo-[a,d]cycloheptene-3-thioamide (5.5 g., 0.021 mole) and ethyl 4-chloroacetoacetate (6.7 g., 0.042 mole) in ethanol (5.0 ml.) is heated at reflux for 24 hours. After cooling the product is obtained by filtration (7.1 g, m.p. 107°–109° C.). Recrystallization from ethanol gives 6.45 g, m.p. 108°–110° C.

Elemental analysis for C$_{22}$H$_{19}$NO$_3$S: Calcd.: C, 70.00; H, 5.07; N, 3.71; Found: C, 70.04; H, 5.11; N, 3.68.

Step 3:
2-(10,11-Dihydro-5H-5-oxodibenzo[a,d]-cyclohepten-3-yl)thiazole-4-acetamide A mixture of 2-(10,11-dihydro-5H-5-oxodibenzo-[a,d]cyclohepten-3-yl)thiazole-4-acetic acid ethyl ester (6.0 g, 0.016 mole) in concentrated ammonium hydroxide (50 ml) and dioxane (10 ml) in a pressure bottle is heated at 60° C. for 3 days. After cooling and filtration the title compound is obtained (4.0 g) m.p. 171°–173° C.

Elemental analysis for C$_{20}$H$_{16}$N$_2$O$_2$S: Calcd.: C, 68.94; H, 4.63; N, 8.04. Found: C, 69.21; H, 4.60; N, 7.95.

Step 4:
4-[2-(10,11-Dihydro-5H-5-oxodibenzo[a,d]cyclohepten-3-yl)-4-thiazolyl]-3-hydroxy-3-pyrroline-2,5-dione To a mixture of 2-(10,11-dihydro-5H-5-oxodibenzo-α[a,d]cyclohepten-3-yl)thiazole-4-acetamide (3.65 g., 0.0105 mole) and diethyloxalate (1.75 g, 0.012 mole) in dimethylformamide (50 ml.) is added in portions over 15 minutes solid potassium tert-butoxide (2.7 g., 0.024 mole). The mixture is allowed to stand at room temperature for 1–4 days. After pouring into water (300 ml.) and acidification with hydrochloric acid a yellow solid is obtained (3.5 g.). Purification by dissolving in warm dimethylformamide (30 ml), concentration to half volume and addition of acetonitrile provides the title product (2.2 g) m.p. 282°–284° C. Further purification by repeating this procedure gives 1.6 g of analytically pure product, m.p. 284°–285° C.

Elemental analysis for C$_{22}$H$_{14}$N$_2$O$_4$S; Calcd: C, 65.66, H, 3.51, N, 6.96. Found: C, 65.57, H, 3.41; N, 7.00.

When the procedure of Example 1 is carried out starting with 5H-5-oxodibenzo[a,d]cylohептene-3-carbonitrile, there is obtained 4-[2-(5H-5-oxodibenzo[a,d]cycloheptene-3-yl)-4-thiazolyl]-3-hydroxy-3-pyrroline-2,5-dione.

When the procedure of Example 1 is followed, except that 3-bromo-4-oxobutanoic acid ethyl ester is employed in place of ethyl 4-chloroacetoacetate in Step 2, there is obtained 4-[2-(10,11-dihydro-5H-5-oxodibenzo[a,d]cyclohepten-3-yl)-5-thiazolyl]-3-hydroxy-3-pyrroline-2,5-dione.

EXAMPLE 2

Preparation of 4-[2-[2-(10,11-dihydro-5H-5-oxodibenzo[a,d]-cycloheptene-3-yl)-4-thiazolyl]ethyl]-3-hydroxy-3-pyrroline-2,5-dione

Step 1:
4-[2-(10,11-Dihydro-5H-5-oxodibenzo[a,d]cyclohepten-3-yl)-4-thiazolyl]butanenitrile A mixture of 10,11-dihydro-5H-5-oxodibenzo[a,d]cyclohepten-3-thioamide (2.67 g., 0.01 mole) and 6-chloro-5-oxohexanenitrile (2.28 g., 0.012 mole) is heated at 60° C. in toluene for 24 hours. On cooling and partial evaporation there is obtained the above intermediate.

Step 2:
2-Oxo-3-cyano-5-[2-10,11-dihydro-5H-5-oxodibenzo[a,d]cyclohepten-3-yl)-4-thiazolyl]butanenitrile To the product of Step 1 (3.58 g., 0.01 mole) in dimethylformamide (40 ml.) is added diethyl oxalate (1.74 g., 0.012 mole) and potassium t-butoxide (2.48 g., 0.022 mole). The mixture is stirred overnight. Following evaporation under vacuum to one half volume, chloroform (400 ml.) is added, plus water (200 ml.) and the mixture acidified with conc. HCl to pH 2–3. The chloroform is separated and washed well with water. The chloroform extract on evaporation provides the above-named intermediate.

Step 3:
4-[2-[2-(10,11-dihydro-5H-5-oxodibenzo[a,d]cyclohepten-3-yl)-4-thiazolyl]ethyl]-3-hydroxy-3-pyrroline-2,5-dione The ester product of Step 2 (2.26 g., 0.005 mole) is dissolved in methanesulfuric acid (25 ml.) and the mixture stirred overnight. To the mixture is added 80% ethanol-water (200 ml.). After standing for two hours, the ethanol is partially removed by evaporation to give the title compound.

When the reactions of Example 2 are carried out using 5H-5-oxodibenzo[a,d]cycloheptene-3-thioamide as starting material there is obtained 4-[2-[2-(5H-5-oxodibenzo[a,d]-cyclohepten-3-yl)-4-thiazolyl]ethyl]-3-hydroxy-3-pyrroline-2,5-dione.

EXAMPLE 3

Preparation of 2-(10,11-dihydro-5H-5-oxodibenzo[a,d]cyclohepten-3-yl)acetonitrile To 2-[2-(10,11-dihydro-5H-5-oxodibenzo[a,d]cyclohepten-3-yl]acetamide (3.48 g., 0.01 mole) in pyridine (30 ml.) is added gradually p-toluenesulfonyl chloride (1.91 g., 0.01 mole). After stirring for 2 hours, the mixture is poured into excess ice-water to give the title compound.

Included within the scope of the invention are the pharmaceutically acceptable salts of formula (I) compounds. The compounds of formula (I) are strong organic acids with a pKa in the range 2–4. These salts are readily formed with the usual inorganic cations such as sodium, potassium and ammonium. Salts with organic amines such as trimethylamine, triethylamine, n-butylamine and the like are also very stable. The neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt.

The compounds of formula (I) are utilized for the stated utilities by formulating them in a composition such as tablet, capsule or elixir for oral administration. Sterile solutions or suspensions can be used for parenteral administration. About 10 to 200 mg of a compound of formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose will be in the 30 to 2000 mg. range, and preferably in the 50 to 1000 mg. range.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coating or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

What is claimed is:

1. The compounds having the structure:

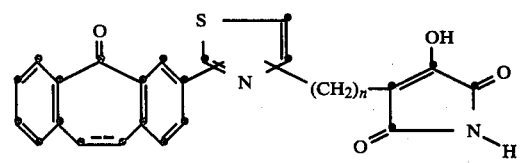

wherein n is 0 to 2, the dotted line indicates saturation or unsaturation or pharmaceutically acceptable salts thereof with the proviso that the substituents on the thiazolyl ring are not adjacent.

2. The compounds according to claim 1 wherein n is 0; having the structure:

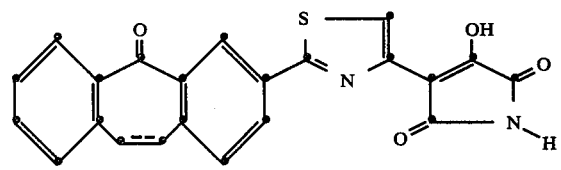

wherein the dotted line indicates saturation or unsaturation or a pharmaceutically acceptable salt thereof.

3. The compound according to claim 1 having the structure:

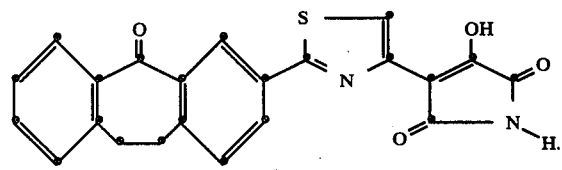

4. A pharmaceutical composition useful in preventing the formation of calcium oxalate kidney and bladder stones comprising an effective amount of a compound of claim 1 or a pharmaceutically acceptable salt thereof and a pharmaceutically acceptable carrier.

5. A pharmaceutical composition useful in preventing the formation of calcium oxalate kidney and bladder stones comprising an effective amount of the compound of claim 3.

6. A method of treating persons afflicted with with calcium oxalate renal lithiasis or preventing the formation of calcium oxalate kidney or bladder stones which comprises administration to such patients an effective amount of compound having the structure:

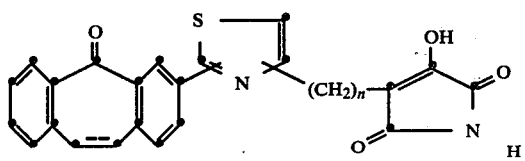

wherein n is 0 to 2, the dotted line indicates saturation or unsaturation or pharmaceutically acceptable salts thereof with the proviso that the substituents on the thiazolyl ring are not adjacent.

7. A method of treating persons afflicted with calcium oxalate renal lithiasis or preventing the formation of calcium oxalate kidney or bladder stones which comprises administration to such patients an effective amount of compound having the structure:

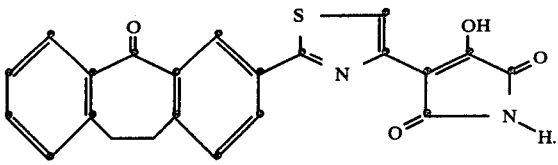

* * * * *